United States Patent
Nixdorf et al.

(10) Patent No.: US 11,448,714 B2
(45) Date of Patent: Sep. 20, 2022

(54) MULTI-PLANAR INTRAORAL RF COIL FOR MAGNETIC RESONANCE IMAGING

(71) Applicant: REGENTS OF THE UNIVERSITY OF MINNESOTA, Minneapolis, MN (US)

(72) Inventors: Donald Robert Nixdorf, Minneapolis, MN (US); Ali Caglar Ozen, Minneapolis, MN (US); Djaudat Idiyatullin, Minneapolis, MN (US); Gregor Adriany, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 16/933,855

(22) Filed: Jul. 20, 2020

(65) Prior Publication Data

US 2021/0018579 A1 Jan. 21, 2021

Related U.S. Application Data

(60) Provisional application No. 62/875,884, filed on Jul. 18, 2019.

(51) Int. Cl.
*G01R 33/34* (2006.01)
*A61B 5/055* (2006.01)
*A61C 19/04* (2006.01)

(52) U.S. Cl.
CPC ........ *G01R 33/34092* (2013.01); *A61B 5/055* (2013.01); *A61C 19/04* (2013.01); *G01R 33/34084* (2013.01)

(58) Field of Classification Search
CPC ............ G01R 33/34084; G01R 33/341; G01R 33/3415; G01R 33/3806; G01R 33/34092;
(Continued)

(56) References Cited

U.S. PATENT DOCUMENTS

| 9,541,615 B2 | 1/2017 | Idiyatullin |
| 2011/0130647 A1 | 6/2011 | Swartz |

(Continued)

FOREIGN PATENT DOCUMENTS

WO WO-2010142760 A2 * 12/2010 ........... G01R 33/383

OTHER PUBLICATIONS

English translation of WO 2010142760 provided by Espacenet. 2021 (Year: 2021).*

(Continued)

*Primary Examiner* — Rishi R Patel
(74) *Attorney, Agent, or Firm* — Quarles & Brady LLP

(57) ABSTRACT

A multi-planar intraoral radio frequency (RF) coil apparatus for use in a magnetic resonance imaging system can include a housing having a shape configured to be positioned in an occlusal plane between an upper jaw and a lower jaw of a subject and a plurality of coil elements disposed within the housing. The plurality of coil elements includes a first coil element positioned in a first plane and a second coil element positioned in a second plane different from the first plane and substantially parallel to the first plane. The coil elements can be loop coil elements or dipole coil elements.

18 Claims, 11 Drawing Sheets

(58) Field of Classification Search
CPC ... G01R 33/3678; A61B 5/055; A61B 5/4542; A61B 5/4547; A61B 5/682; A61C 19/04; A61C 9/0046
See application file for complete search history.

(56) References Cited

U.S. PATENT DOCUMENTS

| | | | | |
|---|---|---|---|---|
| 2012/0146645 | A1* | 6/2012 | Rasche | G01R 33/421 324/318 |
| 2012/0288820 | A1* | 11/2012 | Choe | A61B 5/682 433/29 |
| 2013/0190608 | A1* | 7/2013 | Schmidt | G01R 33/341 600/422 |
| 2014/0084923 | A1* | 3/2014 | Grodzki | G01R 33/561 324/309 |
| 2014/0213888 | A1* | 7/2014 | Idiyatullin | G01R 33/34084 600/422 |
| 2016/0349336 | A1* | 12/2016 | Chang | G01R 33/34046 |

OTHER PUBLICATIONS

Bracher A-K, et al. Ultrashort echo time (UTE) MRI for the assessment of caries lesions. Dentomaxillofacial Radiol. 2013;42:20120321 doi: 10.1259/dmfr.20120321.

Idiyatullin D, et al. Intraoral approach for imaging teeth using the transverse B 1 field components of an occlusally oriented loop coil. Magn. Reson. Med. 2014;72:160-165 doi: 10.1002/mrm.24893.

Idiyatullin D, et al. Dental Magnetic Resonance Imaging: Making the Invisible Visible. J. Endod. 2011;37:745-752 doi: 10.1016/j.joen.2011.02.022.

Idiyatullin D, et al. Role of MRI for detecting micro cracks in teeth. Dentomaxillofacial Radiol. 2016;45 doi: 10.1259/dmfr.20160150.

Ludwig U, et al. Dental MRI using wireless intraoral coils. Sci. Rep. 2016;6:23301 doi: 10.1038/srep23301.

Prager M, et al. Dental MRI using a dedicated RF-coil at 3 Tesla. J. Cranio-Maxillofacial Surg. 2015;43:2175-2182 doi: 10.1016/j.jcms.2015.10.011.

Sadeghi-Tarakameh A, et al. A New Coil Element for Highly-Dense Transmit Arrays : An Introduction to Non-Uniform Dielectric Substrate (NODES) Antenna. In: Proc. Intl. Soc. Mag. Res. Med. 27. Montreal, Quebec; 2019. p. 732.

Sedlacik J, et al. Optimized 14+1 receive coil array and position system for 3D high-resolution MRI of dental and maxillomandibular structures. Dentomaxillofacial Radiol. 2015;45:2-7 doi: 10 1259/dmfr.20150177.

Tymofiyeva O, et al. In vivo MRI-based dental impression using an intraoral RF receiver coil. Concepts Magn. Reson. Part B Magn. Reson. Eng. 2008;33B:244-251 doi: 10.1002/cmr.b.20126.

Weiger M, et al. High-resolution ZTE imaging of human teeth. NMR Biomed. 2012;25:1144-1151 doi: 10.1002/nbm.2783.

* cited by examiner

MULTI-PLANAR INTRAORAL RF COIL FOR MAGNETIC RESONANCE IMAGING

CROSS-REFERENCE TO RELATED APPLICATION

This application is based on, claims priority to, and incorporates herein by reference in its entirety U.S. Ser. No. 62/875,884 filed Jul. 18, 2019, and entitled "Combined Intraoral and Face MRI Coil."

STATEMENT REGARDING FEDERALLY SPONSORED RESEARCH

This invention was made with government support under S10-RR023730, P41-EB027061, P41-EB015894 and S10-RR027290 awarded by the National Institutes of Health. The government has certain rights in the invention.

FIELD

The present disclosure relates generally to the field of magnetic resonance imaging and, in particular, to multi-planar intraoral RF coils and methods for dental magnetic resonance imaging.

BACKGROUND

When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped," into the x-y plane to produce a net transverse magnetic moment $M_t$. A signal is emitted by the excited nuclei or "spins", after the excitation signal $B_1$ is terminated and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well-known reconstruction techniques.

MRI-based techniques are increasingly preferred over other imaging modalities in clinical medicine, for example, due to growing healthcare concerns over cumulative exposure to ionizing radiation, as is used in x-ray and computed tomography (CT) imaging. Even in dentistry applications, wherein x-ray has been a mainstay of clinical practice, MRI is growing in popularity. Beyond the avoidance of ionizing radiation, MR techniques for diagnostic imaging in dentistry have become of greater interest due to new advances that have enabled direct imaging of densely calcified tissues of the human body, such as dentin and enamel. These tissues have low water content and, thus, a low fraction of protons to obtain signal from or MRI imaging. Also, these tissues have a quickly decaying signal and, thus, very short transverse relaxation times. $T_2$. In other words, the signal from mineralized dental tissue decays before MRI signal digitization occurs, resulting in MM images with little or no image intensity. However, currently, there are at least four different and clinically viable MRI methods for obtaining these images of densely calcified dental tissue, these include: I) Ultrashort TE (UTE), ii)Seep Imaging with Fourier Transformation (SEIFT), iii) FID-projection imaging also called BLAST, RUFIS, WASPI, or zero TE (ZTE), and iv) combined PETRA techniques.

In bone, the rapid decay of the MR signal requires an increase in the encoding bandwidth. For bone MM, FIS-based imaging methods have been proposed, which are limited by finite acquisition delays, i.e., dead time, and bandwidth die to limited RF power and amplifier performance, and the gradient slew rates. Imaging techniques such as SWIFT and its variants use a frequency-modulated excitation and a simultaneous acquisition to acquire signal from tissue with very short T2 or T2*. All these pulse sequences are based on radial encoding, and cannot use slice- or slab-selective pulses to preserve signal from tissue with ultra-short T2. Thus, the acquired field-of-view (FOV) must include the entire sensitive volume of the RF coil to avoid aliasing. The resolution of an image voxel depends on the FOV and the reconstructed matrix size. Large FOV would result in an increase in the acquired signal matrix size and in the required number of radial views, thus longer scan times to achieve the desired image resolution. SNR is proportional to Larmor frequency (i.e., field strength), $\omega_0$, voxel volume, V, and acquisition time, $T_{acq}$:

$$SNR \propto \omega_0 V \sqrt{T_{acq}} \qquad (1)$$

The SNR provided by a coil is essentially proportional to the geometric filling factor, $\eta$, which is a measure of the fraction of RF coil volume occupied by the sample, and the quality factor, Q, of the coil:

$$SNR \propto \eta Q \qquad (2)$$

Although there is a clinical need for dental MRI, and advanced pulse sequences for bone imaging such as SWIFT can be implemented in mode of the clinical MM systems, commercially available RF coils are often not compatible with the dental anatomy.

In dental MRI, submillimeter structures (e.g., small fractures within dental roots) must be resolved. To achieve this high resolution within clinically acceptable measurement times, the image field-of-view FOV) must be restricted to the target region which can be realized by a small RF excitation field $B_1^+$, a limited receive sensitivity $B_1^-$, or a combination of both. Extraoral surface coils and coil arrays are typically been used for dental MRI, however, extraoral coils have limited resolution and sensitivity and are expensive. For an average-sized patient, the distance between an extraoral coil element and a molar is about 30-50 mm, which reduces the sensitivity significantly. In addition, with an extraoral configuration, the cheek and buccal fat produce intense signal. As a result, the signal from these unwanted tissue dominates the images. To overcome this limitation, an intraoral coil was proposed that is positioned between the teeth and cheek, i.e., the buccal vestibule, which increases both resolution and SNR. Shielding may be added to this intraoral coil configuration to eliminate the intense signal from the cheek, however, the addition of shielding sacrifices patient comfort, as well as SNR. An inductively coupled intraoral coil was developed that may be used to image a single tooth and to be used with external coil elements. The tuning of the coil for each patient is challenging as it cannot be modified once the coil is sealed. Furthermore, these coils can only acquire MR signal from the apices of posterior teeth due to anatomical constraints. For better coverage and patient comfort, an intraoral loop coil with the end plane orthogonal to $B_0$ was developed, where the transverse $B_1$ fields are sensitive to MR signal. The sensitive volume of the loop coil included the most important dental structures, such as the teeth and jaws, and mostly excluded cheeks and lips. However, the sensitive depth did not reach the roots of molar teeth, and the loop obstructed the tongue movement resulting in patient discomfort.

It would be desirable to provide an intraoral RF coil that provides increased depth of sensitivity e.g., to allow imaging of the roots of the teeth, as well improves patient comfort.

SUMMARY OF THE DISCLOSURE

In accordance with an embodiment, a multi-planar intraoral radio frequency (RF) coil apparatus for use in a magnetic resonance imaging system can include a housing having a shape configured to be positioned in an occlusal plane between an upper jaw and a lower jaw of a subject and a plurality of coil elements disposed within the housing. The plurality of coil elements includes a first coil element positioned in a first plane and a second coil element positioned in a second plane different from the first plane and substantially parallel to the first plane.

In accordance with another embodiment a radio frequency (RF) coil apparatus for use in a magnetic resonance imaging system includes an extraoral RF coil configured to be positioned on a surface of a subject and a multi-planar intraoral RF coil. The multi-planar intraoral RF coil includes a housing having a shape configured to be positioned in an occlusal plane between an upper jaw and a lower jaw of the subject and a plurality of coil elements disposed within the housing. The plurality of coil elements includes a first coil element positioned in a first plane; and a second coil element positioned in a second plane different from the first plane and substantially parallel to the first plane.

In accordance with another embodiment, a magnetic resonance imaging (MRI) system includes a magnet system configured to generate a polarizing magnetic field about at least a portion of a subject, magnetic gradient system including a plurality of magnetic gradient coils configured to apply at least one magnetic gradient field to the polarizing magnetic field and a radio frequency (RF) system configured to apply an RF field to the subject and to receive magnetic resonance signals from the subject using at least one RF coil. The at least one RF coil is a multi-planar intraoral RF coil and includes a housing having a shape configured to be positioned in an occlusal plane between an upper jaw and a lower jaw of the subject and a plurality of coil elements disposed within the housing. The plurality of coil elements includes a first coil element positioned in a first plane and a second coil element positioned in a second plane different from the first plane and substantially parallel to the first plane.

BRIEF DESCRIPTION OF THE DRAWINGS

The present disclosure will hereafter be described with reference to the accompanying drawings, wherein like reference numerals denote like elements.

DETAILED DESCRIPTION

Figure 1:
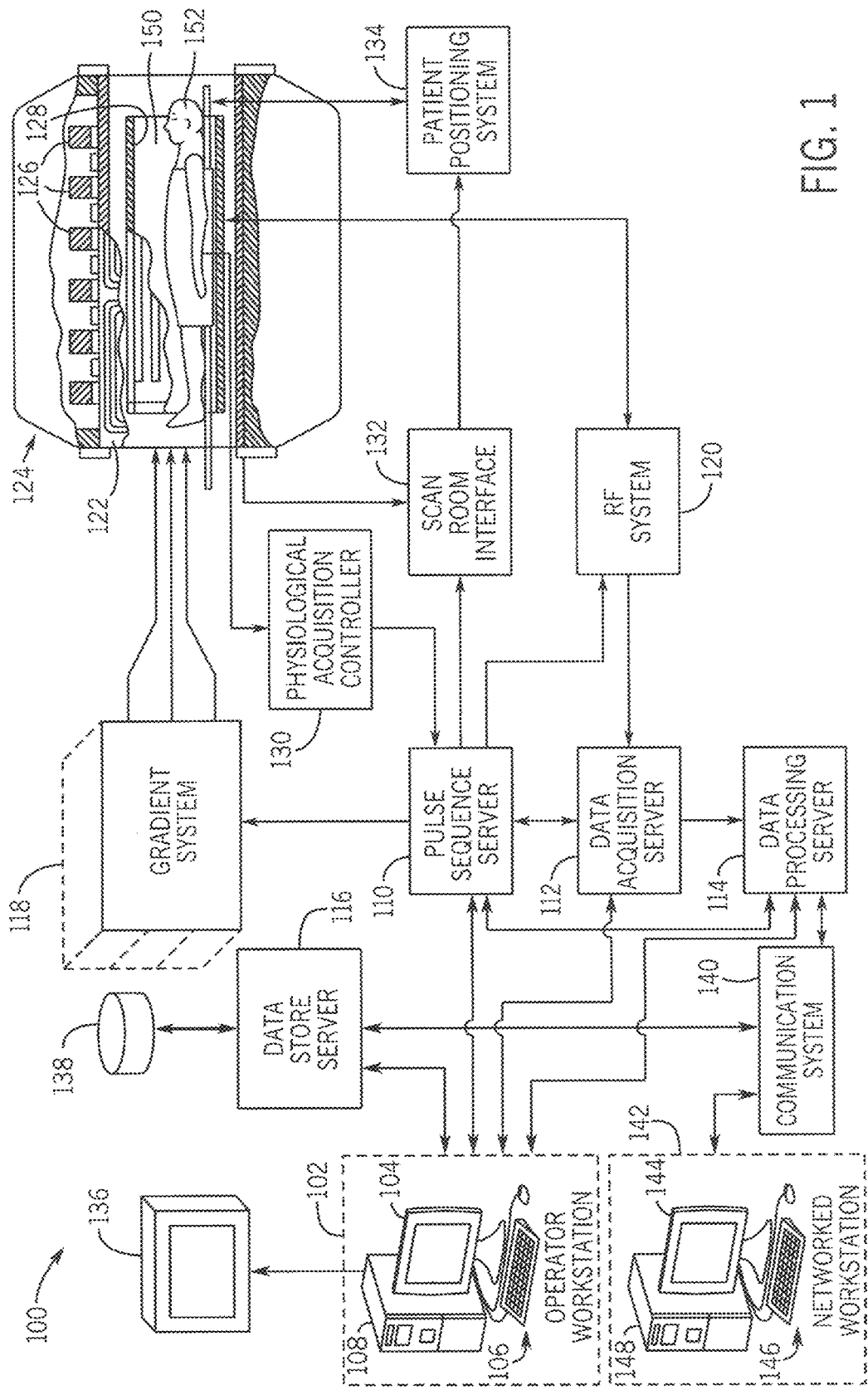
FIG. 1 is a schematic diagram of an example MRI system in accordance with an embodiment.

FIG. 1 shows an example of an Mill system 100. Mill system 100 includes an operator workstation 102, which may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MM pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \quad (3)$$

and the phase of the received magnetic resonance signal may also be determined according to the following relationship:

$$\varphi = \tan^{-1}\left(\frac{Q}{I}\right). \quad (4)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MIRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

In FIG. 1, magnet assembly 124 is cylindrical in shape and surrounds an imaging volume 150 within a patient bore tube (not shown). A subject (e.g., a patient or object) 152 is positioned within the imaging volume 150. A main magnetic field $B_0$ (or polarizing field) is oriented along a longitudinal axis of the imaging volume 150 within the cylindrical patient bore. While the embodiment shown in FIG. 1 shows a cylindrical magnet assembly, it should be understood that the local multi-planar intraoral RF coils of the present disclosure may be used with systems having other topologies than a cylindrical assembly, such as, for example, open or vertical (upright) MRI systems. In an open or vertical MM system, the main magnetic field $B_0$ is vertically oriented with respect to the magnet system. The disclosed multi-planar intraoral RF coils may be used with a general purpose or specialized MRI system. The present disclosure describes various embodiments of multi-planar intraoral radio frequency (RF) coils configured to provide an increased depth of sensitivity as well as to facilitate patient comfort. The disclosed multi-planar intra-oral coils may include two or more coil elements, each of which is provided in a different plane, for example, in an overlapping or stacked arrangement. The two or more coil elements may be loop coil elements or dipole coil elements. In some embodiments, the multi-planar intraoral coil has a size and shape to be positioned between the teeth of an upper jaw and a lower jaw in an occlusal plane. For example, the coil elements of the multi-planar intraoral RF coil may be disposed in a housing configured as a dental plate. In another example, the coil elements are disposed in a housing configured as a dental impression tray which has the advantage of positioning some of the coil elements around the teeth and extending the depth of sensitivity toward the roots. In another embodiment, the multi-planar intraoral RF coil positioned in the occlusal plane is used in combination with an extraoral coil positioned on a surface of the subject (e.g., the face of a patient). The various embodiments of the multi-planar intraoral RF coil have a number of advantages such as allowing for imaging a region of interest (e.g., areas of the face) with a smaller field of view which can result in higher resolution, faster scan times and avoids imaging unnecessary structures. In addition, the disclosed multi-planar intraoral RF coil provides improved signal capture from the dentoalveolar tissues, homogeneous sensitivity across these varied tissues, and minimizes the problem of coupling between coil elements.

The disclosed multi-planar intraoral RF coil may be used for MR imaging of dental anatomy including, but not limited to, jaws, cranial nerves within the face, salivary glands, facial bones, teeth and roots. In various embodiments, the multi-planar intraoral RF coil may be used in an MM system to acquire data and images to detect vertical root fractures and the blood flow in teeth. Dental imaging may be also be used for applications such as pre-surgical planning, implant planning, assessment of dental and periapical anatomy an pathology, localization of impacted teeth, evaluation of dental vitality, tumor detection, imaging of the morphology and function of the temporomandibular joint.

Figure 3:
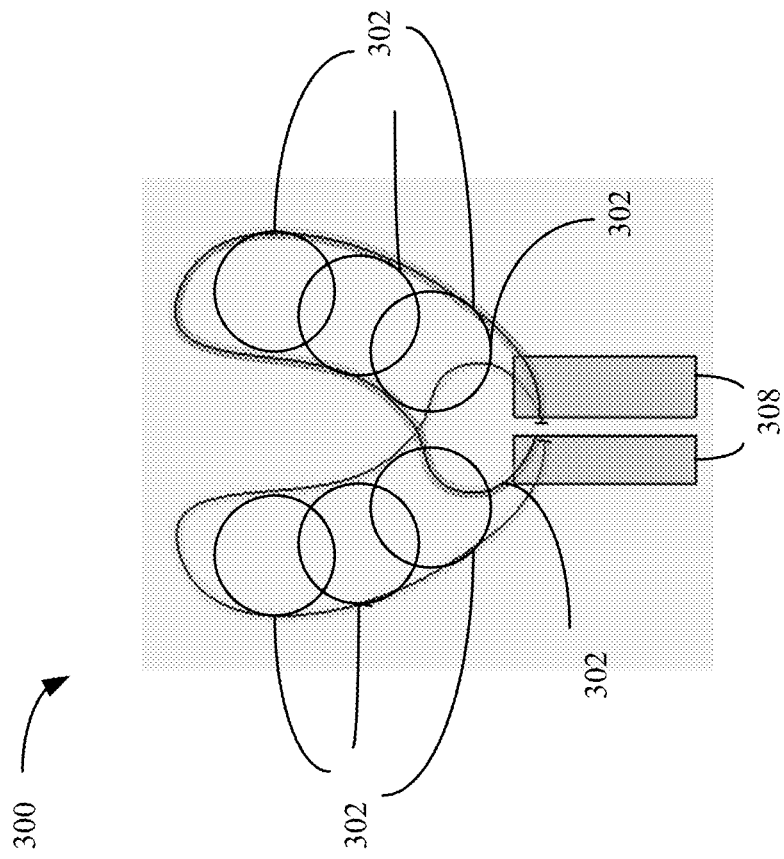
FIG. 3 is a diagram of a multi-planar loop intraoral radio frequency (RF) coil having multiple overlapping coil elements in accordance with an embodiment.
Figure 2:
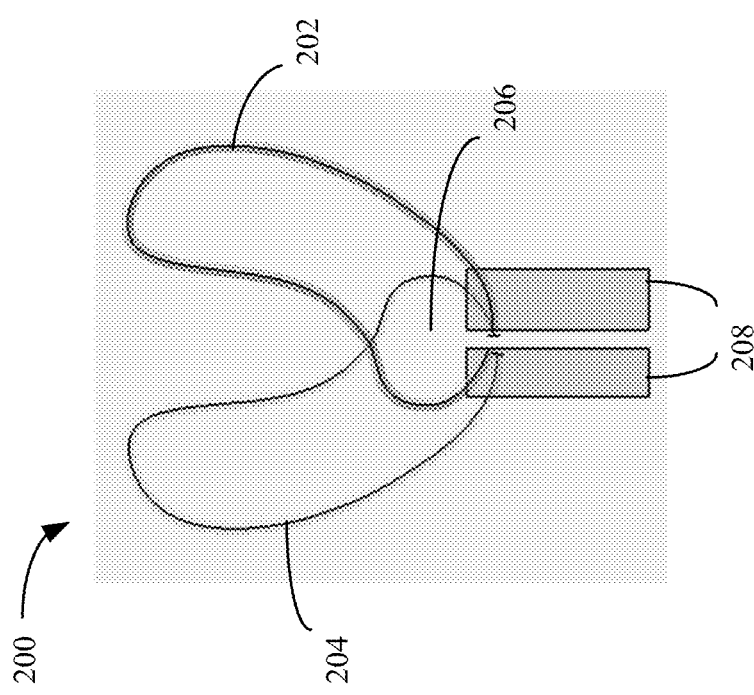
FIG. 2 is a diagram of a multi-planar loop intraoral radio frequency (RF) coil having overlapping coil elements in accordance with an embodiment.

FIGS. 2-6 are diagrams of various embodiments of a multi-planar loop intraoral radio frequency (RF) coil. In FIG. 2, a multi-planar loop intraoral coil 200 includes a first coil element 202 and a second coil element 204. The first coil element 202 and second coil element 204 are formed as loops that have an area of overlap 206. In the area of overlap, the second coil element 204 may be positioned above or below the first coil element 202 in a plane parallel or substantially parallel to a plane of the first coil element 202. The first coil element 202 and second coil element 204 may be formed from a single wire or from multiple wires. Each coil element 202, 204 is configured to provide a channel, for example, coil element 202 may provide a channel for the left side of the mandible and coil element 204 may provide a channel for the right side of the mandible. Each of the first coil element 202 and the second coil element 204 are coupled to input ports 208, for example conductor plates. The input ports 208 may also be coupled to a cable and other circuitry as discussed further below with respect to FIGS. 12-13. In another embodiment, the coil 200 may be configured so that the first coil element 202 and the second coil element 204 may be operated separately, for example, one at a time. While the embodiment in FIG. 2 shows the two loops 202 and 204 in a "U" shape, in other embodiments, the loops 202 and 204 may be an "O" shape. In another embodiment, each loop 202, 204 may each be further divided into two or more loops to provide additional channels. In yet another embodiment, a multi-planar intraoral coil 300 may include a plurality of small overlapping loop coil elements 302 as shown in FIG. 3. Each of the plurality of coil elements 302 are coupled to input ports 308, for example conductor plates. An embodiment with more than two loops may be advantageous for use in a vertical (upright) magnet for, for example, higher signal to noise ratio (SNR) and parallel imaging. In an embodiment, the coil elements 202, 204 in FIG. 2 and the coil elements 302 in FIG. 3 may be covered with an insulation and embedded in, for example, a bite plate. As mentioned, the multi-planar intraoral RF coils 200, 300 are configured to be positioned in the occlusal plane between the upper and lower jaw.

Figure 4B:
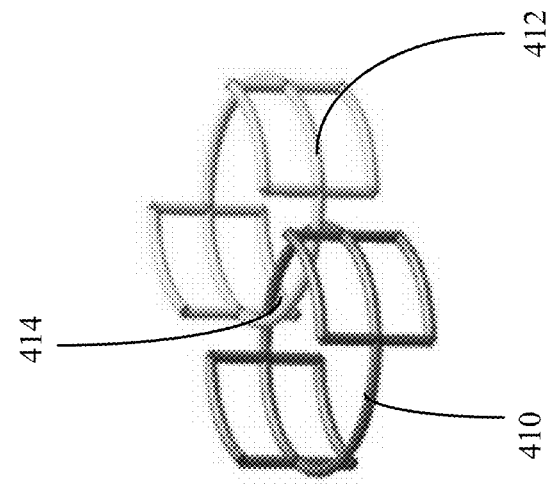
FIG. 4B is a diagram of overlapping loop coils for a multi-planar loop intraoral radio frequency (RF) coil having stacked coil elements in accordance with an embodiment.
Figure 4A:
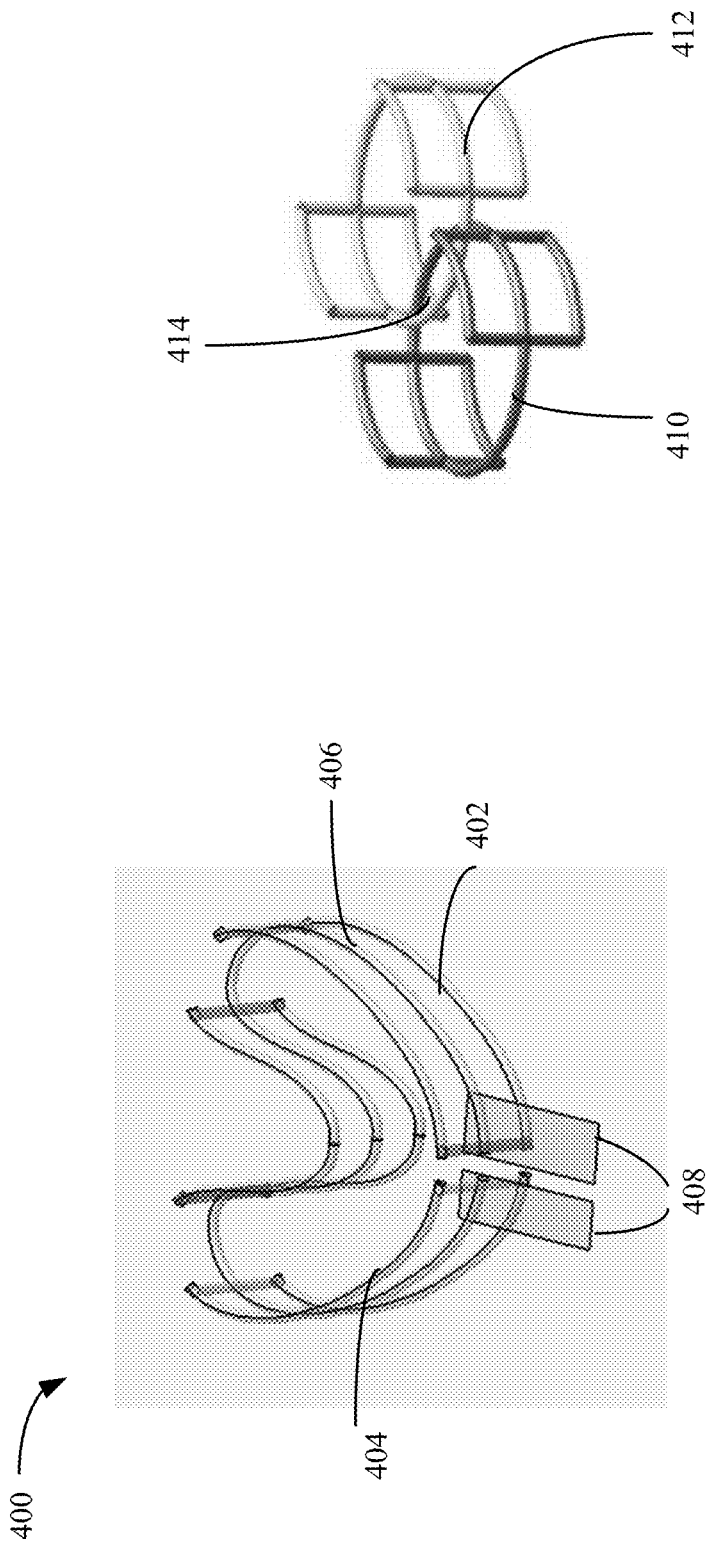
FIG. 4A is a diagram of a multi-planar loop intraoral radio frequency (RF) coil having stacked coil elements in accordance with an embodiment.

FIG. 4A illustrates a multi-planar loop intraoral coil 400 having three coil elements 402, 404 and 406 in a stacked arrangement in accordance with an embodiment. A second coil element 406 may be positioned above the first coil element 402 in a plane parallel to a plane of the first coil element. A third coil element 404 may be positioned above the first coil element 402 and the second coil element 406 in a plane parallel to the plane of the first coil element 402 and the plane of the second coil element 406. In some embodiments, the planes of the first, second and third coil elements 402, 406, 404 are parallel (i.e., the vertical distance between the planes is constant) and in other embodiments, the planes of the first, second and third coil elements 402, 406, 404 are substantially parallel (i.e., the vertical distance between the coil element planes varies, for example, the vertical distance between the coil element planes in the front part (towards the front of the patient's mouth) of the coil 400 is larger than the vertical distance between the coil element planes in the rear part of the coil 400 (where the molar teeth are located)) Each coil element 402, 404, and 406 may be formed from a wire. Each of the first coil element 402, the second coil element 406 and the third coil element 404 are coupled to input ports 408, for example conductor plates. The input ports 408 may also be coupled to a cable and other circuitry as discussed further below with respect to FIGS. 13-14. In an embodiment, the coil elements 402, 404, and 406 may be covered with an insulation and embedded in, for example, a bite plate. In another embodiment, the coil elements 402, 404, and 406 may be covered with an insulation and embedded in a housing configured as a dental impression tray so that the teeth of the upper jaw and the lower jaw may fit in the channel or recess formed by the coil elements 402, 404 and 406. As mentioned, the multi-planar intraoral RF coil is configured to be positioned in the occlusal plane between the upper and lower jaw. In another embodiment, one or more of the coil elements 402, 404 and 406 shown in FIG. 4A may include two or more overlapping loops as shown in FIG. 4B. In FIG. 4B, an exemplary first loop 410 and second loop 412 have an area of overlap 414.

Figure 6:
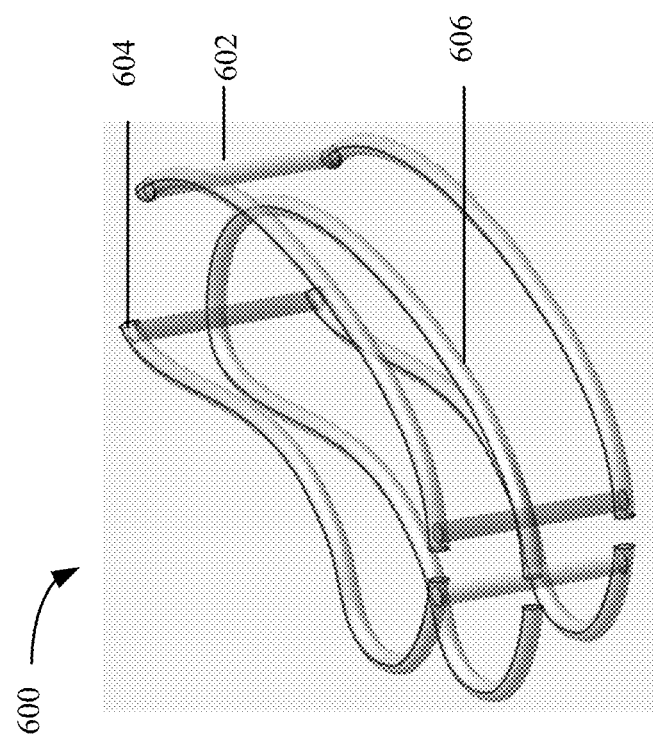
FIG. 6 is a diagram of a multi-channel loop intraoral radio frequency (RF) coil having stacked coil elements in accordance with an embodiment.
Figure 5:
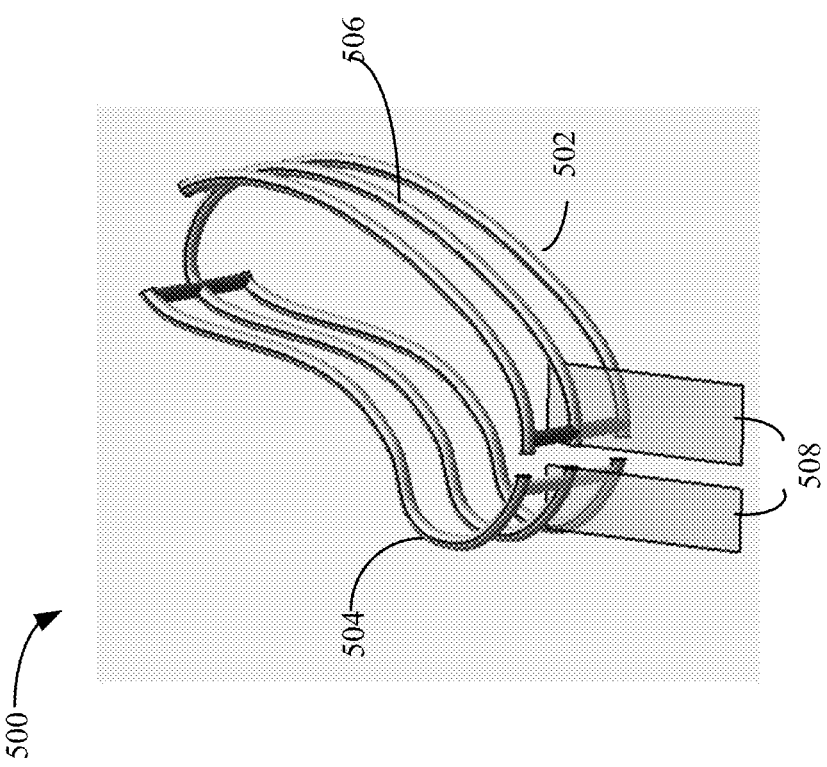
FIG. 5 is a diagram of a multi-planar loop intraoral radio frequency (RF) coil having stacked coil elements in accordance with an embodiment.

In another embodiment, the multi-planar intraoral RF coil may be configured to fit in a portion of the region between the upper jaw and the lower jaw, for example, a portion on one side of the subject's jaw (i.e., the right side or the left side). FIG. 5 is a diagram of a multi-planar loop intraoral radio frequency (RF) coil having stacked coil elements in accordance with an embodiment. In FIG. 5, the multi-planar intraoral RF coil 500 is sized and shaped to cover a portion of the region between the upper jaw and the lower jaw. The coil 500 may provide an increased depth of sensitivity compared to the coil described above with respect to FIG. 4. In the embodiment of FIG. 5, the coil 500 is configured to cover a left side of the region between the upper jaw and a lower jaw. In coil 500, the three coil elements 502, 504, and 506 are in a stacked arrangement. A second coil element 506 may be positioned above the first coil element 502 in a plane parallel or substantially parallel to a plane of the first coil element 502. A third coil element 504 may be positioned above the first coil element 502 and the second coil element 506 in a plane parallel or substantially parallel to the plane of the first coil element 502 and the plane of the second coil element 506. Each coil element 502, 504, and 506 may be formed from a wire. In another embodiment, one or more of the coil elements 502, 504 and 506 may include two or more overlapping loops. The first coil element 502, the second coil element 506 and the third coil element 504 are coupled to input ports 508, for example conductor plates. The input ports 508 may also be coupled to a cable and other circuitry as discussed further below with respect to FIGS. 13-14. In an embodiment, the coil elements 502, 504, and 506 may be covered with an insulation and embedded in, for example, a bite plate. In another embodiment, the coil elements 502, 504, and 506 may be covered with an insulation and embedded in a housing configured as a dental impression tray so that the teeth of the upper jaw and the lower jaw may fit in the channel or recess formed by the coil elements 502, 504 and 506. The multi-planar intraoral RF coil 500 is configured to be positioned in the occlusal plane in a region on one side of the mouth between the upper and lower jaw. In an embodiment, the multi-planar intraoral coil 500 may be configured to provide multiple channels as shown in FIG. 6 where the RF coil 600 includes a first orthogonal loop 602, a second orthogonal loop 604 and a first horizontal loop 606.

In some embodiment, the coil elements of the coils 200, 300, 400, 500 and 600 described above may be constructed from ribbon, segmented ribbon with optimal patterns, wire or a combination of those. In an embodiment, the ribbons or wires may have helical tips to increase the effective wavelength. The coil elements of coils 200, 300, 400, 500 and 600 may be rigid, flexible or reformable semi-rigid cables. In another embodiment, the multi-planar loop intraoral RF coils 200, 300, 400, 500 and 600 may be conformable to the shape of the subject's mouth and teeth. In some embodiments, multi-planar intraoral RF coils may be provided in different sizes for different size jaws and arches. In an embodiment, the insulation material used on the coil elements of coils 200, 300, 400, 500 and 600 may be made of bio-compatible materials and may be patient-specific by using, for example, thermos-plastic materials. In another embodiment, the insulation material may be enriched with MRI-visible contrast agent, for example, for precise registration of the images acquired using the coil 200, 300, 400, 500 or 600 to images from other modalities (e.g., CBCT). In an embodiment, a housing for the coil elements may be 3D printed.

The multi-planar intraoral coils 200, 300, 400, 500 and 600 may be used as transmit-only coils, receive-only coils or transmit and receive coils. In the embodiments described above, the multi-planar combination of coil (or conductor) elements in the form of an impression tray increases the depth of sensitivity. The various embodiments of the multi-planar loop intraoral RF coil 200, 300, 400, 500 and 600 described above with respect to FIGS. 2-5 may provide uniform sensitivity over the teeth and surrounding tissues. The increased penetration depth provides by the multi-planar loop intraoral RF coils described above allows, for example, sensitive detection of the signal from dental roots. In other embodiments, the multi-planar loop intraoral RF coils may minimize coupling with exterior receive coil elements.

Figure 7:
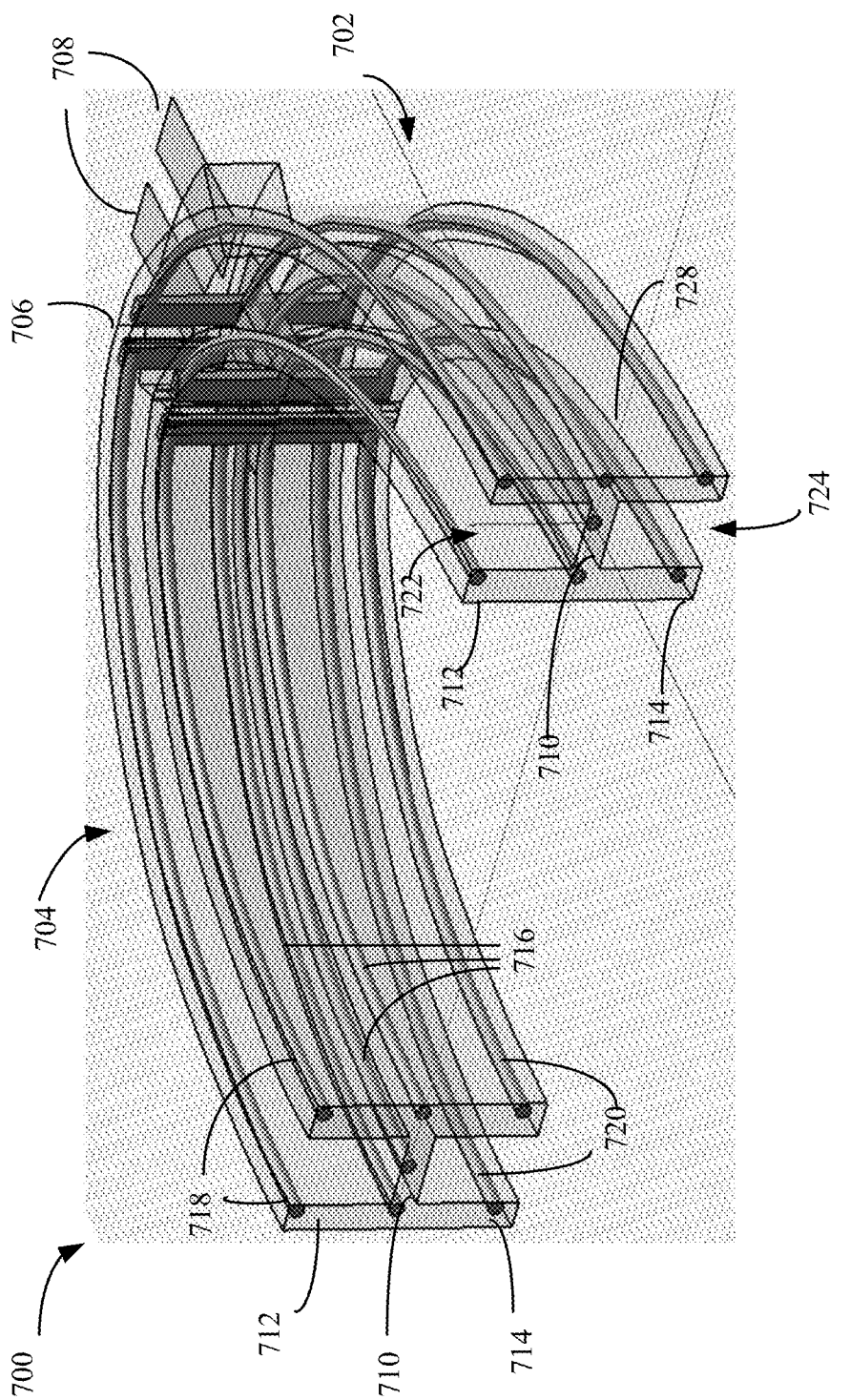
FIG. 7 is a diagram of a multi-planar dipole intraoral radio frequency (RF) coil in accordance with an embodiment.

FIGS. 7-11 are diagrams of various embodiments of a multi-planar dipole intraoral radio frequency (RF) coil. In FIG. 7, a multi-planar dipole intraoral coil 700 includes a first arm 702 and a second arm 704. In the embodiment shown in FIG. 7, the first arm 702 and the second arm 704 have an "H" shape which forms a first (or top) recess or channel 722 and a second (or bottom) recess or channel 724 in which teeth from the upper and lower jaw may be positioned when the coil 700 is positioned in the occlusal plane between the upper jaw and the lower jaw. Accordingly, the shape of the coil 700 may mimic a dental impression tray. In other embodiment, the coil 700 may have other shapes that can provide an upper 722 and a lower 724 channel or recess. Each arm 702 and 704 includes a first coil element 710, a second coil element 712 and a third coil element 714. The first coil element 710 may include multiple wires 716. In the embodiment of FIG. 7, the first coil element has three wires 716. A second coil element 712 may be positioned above the first coil element 710 in a plane parallel or substantially parallel to a plane of the first coil element 710. In an embodiment, when the coil 700 is positioned in the occlusal plane of a subject, the plane of the second coil element 712 may be in a superior position to the plane of the first coil element 710. The second coil element 712 may include a plurality of wires 718, for example, in FIG. 7 the second coil element 712 includes two wires 718. A third coil element 714 may be positioned below the first coil element 710 and the second coil element 712 in a plane parallel or substantially parallel to the plane of the first coil element 710 and the plane of the second coil element 712. In an embodiment, when the coil 700 is positioned in the occlusal plane of a subject, the plane of the third coil element \714 may be in an inferior position to the plane of the first coil element 710. The third coil element 714 may include a plurality of wires 620, for example, in FIG. 7 the third coil element 614 includes two wires 720. The wires 718, 620 from the second coil element 712 and the third coil element 714 may be configured to extend the depth of sensitivity of the coil 700.

Figure 8B:
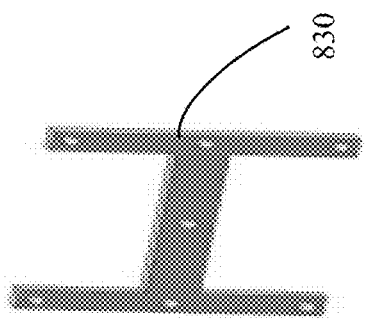
FIG. 8B is a perspective view of a bracket for shorting an end of the multi-planar dipole of FIG. 7A in accordance with an embodiment.
Figure 8A:
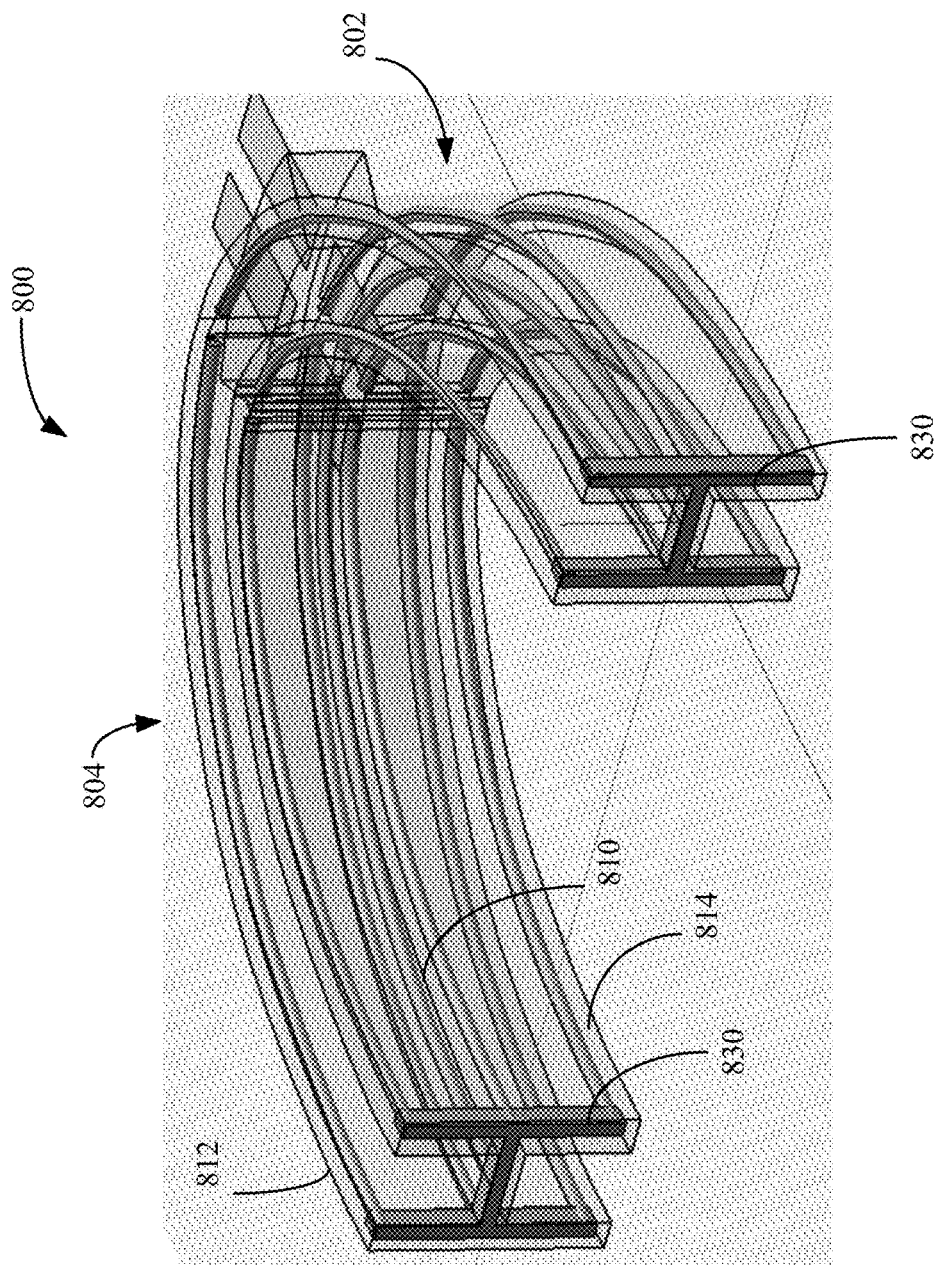
FIG. 8A is a diagram of a multi-planar dipole intraoral radio frequency (RF) coil having a shorted end in accordance with an embodiment.

Each of the first coil element 710, the second coil element 712 and the third coil element 714 are coupled to input ports 708, for example conductor plates. A connector 706 (e.g., a bracket) on the proximal end of the coil 600 may be used to connect the wires 716, 718, 720 in the first arm 702 and the second arm 704. The input ports 708 may also be coupled to a cable and other circuitry as discussed further below with respect to FIGS. 13-14. In an embodiment, the coil elements 710, 712, and 714 may be covered with an insulation and embedded in a housing or former 728. As mentioned, the housing 728 may be configured to have a similar form as a dental impression tray so that the teeth of the upper jaw and the lower jaw may fit in the first channel 722 and the lower channel 724 formed by the coil elements 710, 712 and 714. The multi-planar intraoral RF coil 700 is configured to be positioned in the occlusal plane between the upper and lower jaw. In FIG. 7, the distal end of the first 702 and second 704 arm is open (i.e., not shorted). In an embodiment, the distal ends of the first arm 702 and the second arm 704 may be shorted as shown in FIGS. 8A and 8B. Shorting the distal ends of the first arm 802 and the second arm 804 may increase sensitivity at the distal ends to obtain signal that is towards the back of the mouth. In FIGS. 8A and 8B, an "H-shaped" plate 830 may be attached to the distal end of a first arm 802 and as second arm 804 of the dipole coil 800 to provide shorted ends. The plate 830 may have other shapes based on the shape of the end of the coil 800. The plate 830 may be constructed from a material such as, for example, copper.

Figure 9:
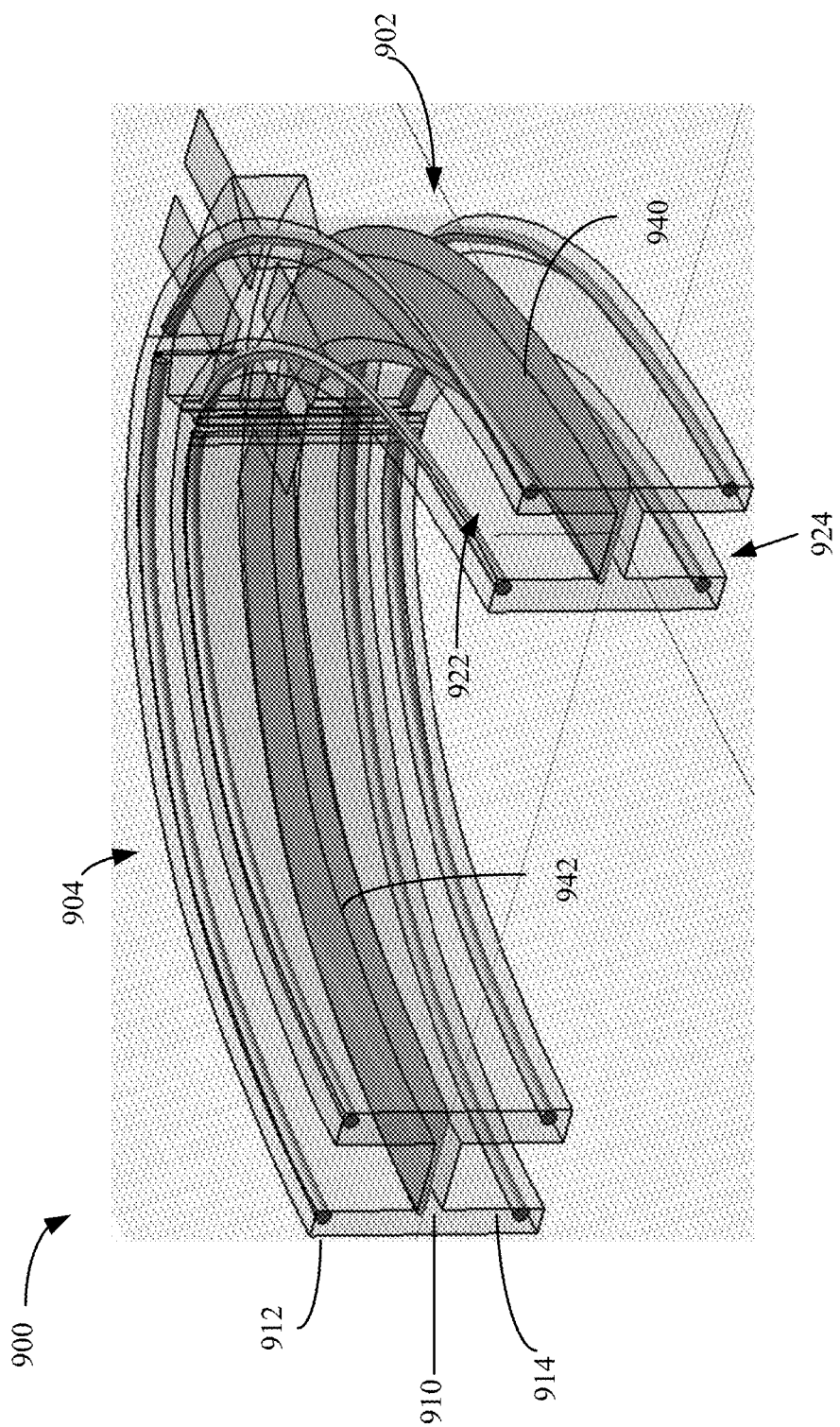
FIG. 9 is a diagram of a multi-planar dipole intraoral radio frequency (RF) coil having a ribbon coil element in accordance with an embodiment.
Figure 10:
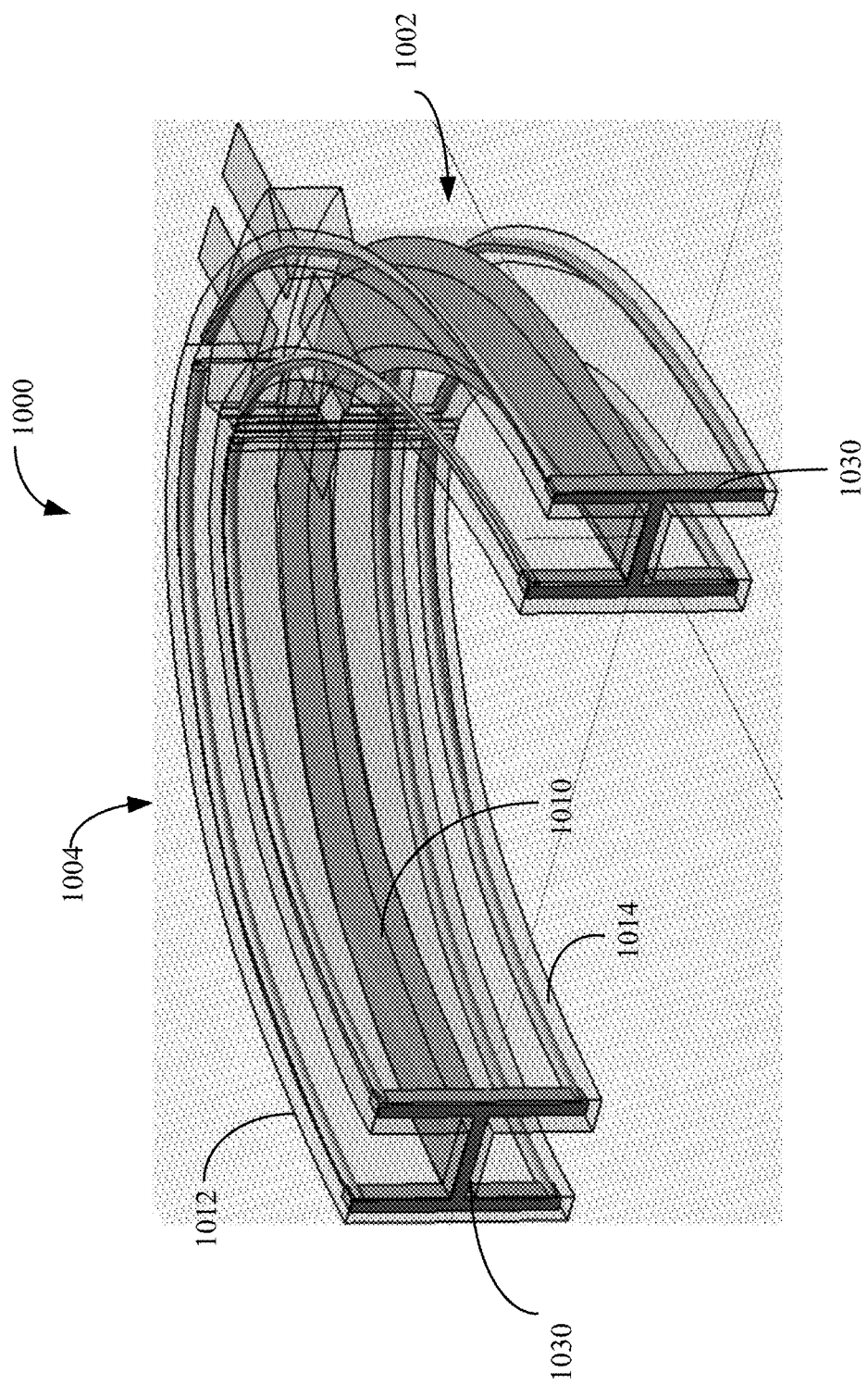
FIG. 10 is a diagram of a multi-planar dipole intraoral radio frequency (RF) coil having a ribbon coil element and a shorted end in accordance with an embodiment.

In another embodiment, at least one of the coil element of a multi-planar intraoral RF coil may be formed from a ribbon as shown in FIGS. 9 and 10. In FIG. 9, a multi-planar intraoral RF coil 900 includes a first arm 902 and a second arm 904. In the embodiment shown in FIG. 9, the first arm 902 and the second arm 904 have an "H" shape which forms a first (or top) recess or channel 922 and a second (or bottom) recess or channel 924 in which teeth from the upper and lower jaw may be positioned when the coil 900 is positioned in the occlusal plane between the upper jaw and the lower jaw. In other embodiment, the coil 900 may have other shapes that can provide an upper 922 and a lower 924 channel or recess. Each arm 902 and 904 includes a first coil element 910, a second coil element 912 and a third coil element 914. The first coil element 910 may include a ribbon 942. The second coil element 912 may be positioned above the first coil element 910 in a plane parallel or substantially parallel to a plane of the first coil element 910. In an embodiment, when the coil 900 is positioned in the occlusal plane of a subject, the plane of the second coil element 92 may be in a superior position to the plane of the first coil element 910. The second coil element 912 and the third coil element 914 may include a plurality of wires as discussed above with respect to FIG. 7. The third coil element 914 may be positioned below the first coil element 910 and the second coil element 912 in a plane parallel or substantially parallel to the plane of the first coil element 910 and the plane of the second coil element 912. In an embodiment, when the coil 900 is positioned in the occlusal plane of a subject, the plane of the third coil element 914 may be in an inferior position to the plane of the first coil element 910. The wires 918, 920 from the second coil element 912 and the third coil element 914 may be configured to extend the depth of sensitivity of the coil 900.

Similar to the embodiments of FIGS. 7 and 8, the coil 900 may be embedded in a housing configured to mimic as a dental impression tray so that the teeth of the upper jaw and the lower jaw may fit in the first channel 922 and the lower channel 924 formed by the coil elements 910, 912 and 914. The multi-planar intraoral RF coil 900 is configured to be positioned in the occlusal plane between the upper and lower jaw. In FIG. 9, the distal end of the first 902 and the second 904 arm are open. In an embodiment, the distal ends of the first arm 902 and the second arm 904 may be shorted as shown in FIG. 10. As mentioned, shorting the distal ends of the first arm 1002 and the second arm 1004 may increase sensitivity at the distal ends to obtain signal that is towards the back of the mouth. In FIG. 10, an "H-shaped" plate 1030 may be attached to the distal end of a first arm 1002 and as second arm 1004 of the dipole coil 1000 to provide shorted ends. The plate 1030 may have other shapes based on the shape of the ends of the coil 1000. The plate 1030 may be constructed from a material such as, for example, copper.

Figure 11:
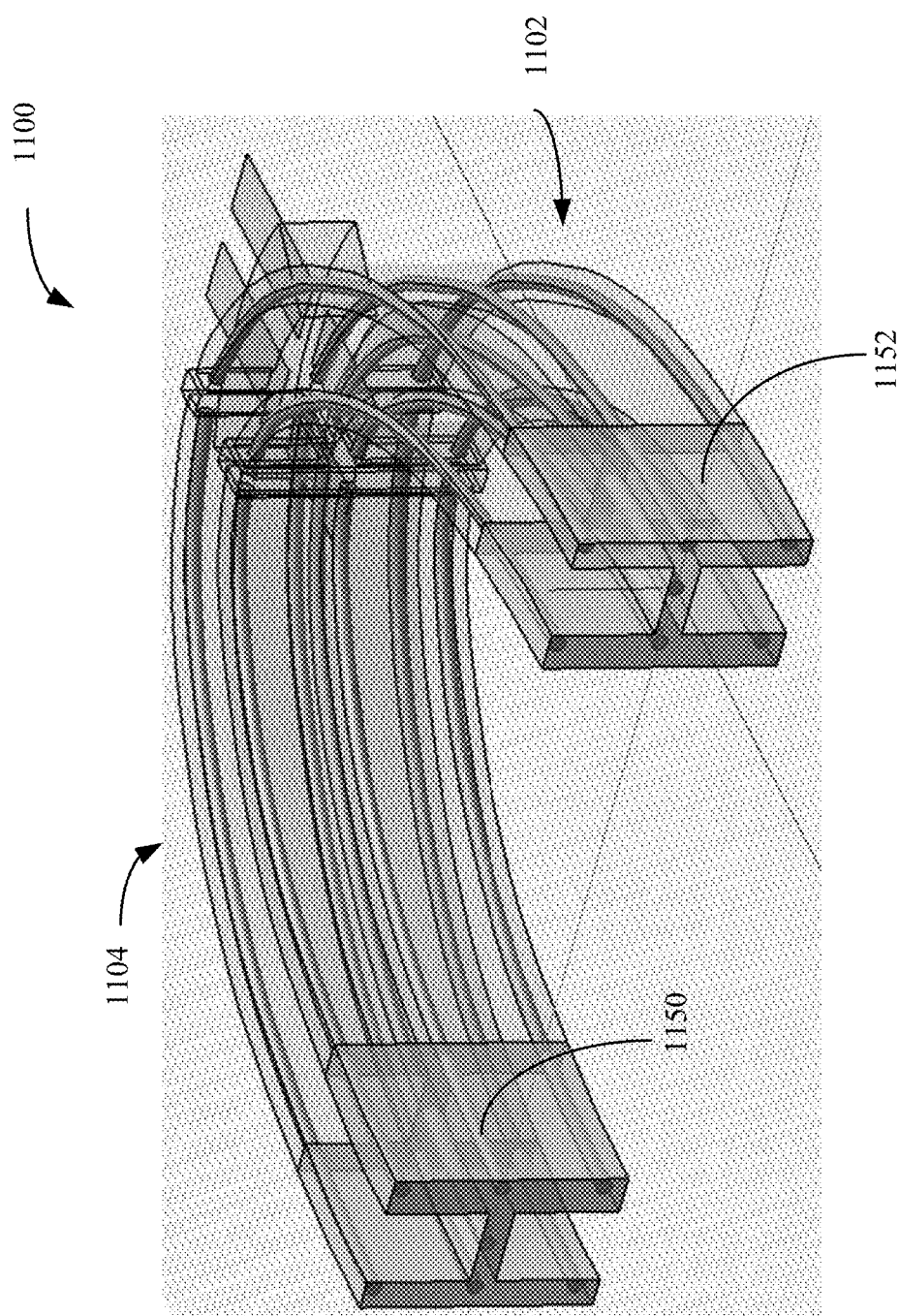
FIG. 11 is a diagram of a multi-planar dipole intraoral radio frequency (RF) coil with a high permittivity dielectric material in accordance with an embodiment.

In another embodiment, a high permittivity material may be included in a multi-planar intraoral RF coil as shown in FIG. 11. The multi-planar dipole coil 1100 includes a first arm 1102 and a second arm 1104. A high permittivity (or high dielectric constant) material 1152 is disposed on the distal end of the first arm 1102 and a high permittivity material 1150 is disposed on the second distal end of the second arm 1104. The high permittivity materials 1150, 1152 may be used within the multi-planar dipole intraoral coil 1100 dipole to produce a more uniform sensitivity throughout the coil 1100. In an embodiment, high permittivity material such as $BaTiO_3$ or $CaTiO_3$ can be used to adjust the impedance at the distal ends of the first 1102 and second 1104 dipole arms. If the permittivity of the materials 1150, 1152 is high, the polarization and, thus the interaction with external fields is stronger. Accordingly, using high permittivity materials 1150, 1152 in the multi-planar dipole RF coil 1100 provides a means of controlling the electric fields and, thus the electromagnetic currents without electrical connection. Current drops rapidly towards the distal end of the dipole arms 1102, 1104 due to high impedance at the tip. Use of an insulation material 1150, 1152 with high relative permittivity (er) around the coil elements (or conductors) increases the capacitance between the dipole arms 1102, 1104 and the body, which reduces the impedance. Reduced impedance enhances the uniformity of the current distribution along the dipole arms 1102, 1104. High permittivity material 1150, 1154 may also be used to reduce SAR. In one embodiment, the high permittivity sections 1150, 1152 can be made of a non-toxic ceramic or another high permittivity bio-compatible compound.

In some embodiment, the coil elements of the coils 700, 800, 900, 1000 and 1100 described above may be constructed from ribbon, segmented ribbon with optimal patterns, wire or a combination of those. In an embodiment, the ribbons or wires may have helical tips to increase the effective wavelength. In another embodiment, wires or ribbons may be extended further at the tips and folded to comply with the anatomy of the subject while increasing the homogeneity along the dipole arm. In an embodiment, meandered wires or ribbon structures may be used to match the effective wavelength of wires used in the dipole arms. The coil elements of coils 700, 800, 900, 1000, and 1100 may be rigid, flexible or reformable semi-rigid cables. In another embodiment, the multi-planar loop intraoral RF coils 700, 800, 900, 1000 and 1100 may be conformable to the shape of the subject's mouth and teeth. In some embodiments, multi-planar intraoral RF coils may be provided in different sizes for different size jaws and arches. In an embodiment, the insulation material used on the coil elements of coils 700, 800, 900, 1000 and 1100 may be made of bio-compatible materials and may be patient-specific by using, for example, thermos-plastic materials. In another embodiment, the insulation material may be enriched with MM-visible contrast agent, for example, for precise registration of the images acquired using the coil 700, 800, 900, 1000 or 1100 to images from other modalities (e.g., CBCT). In an embodiment, a housing for the coil elements may be 3D printed.

Figure 12:
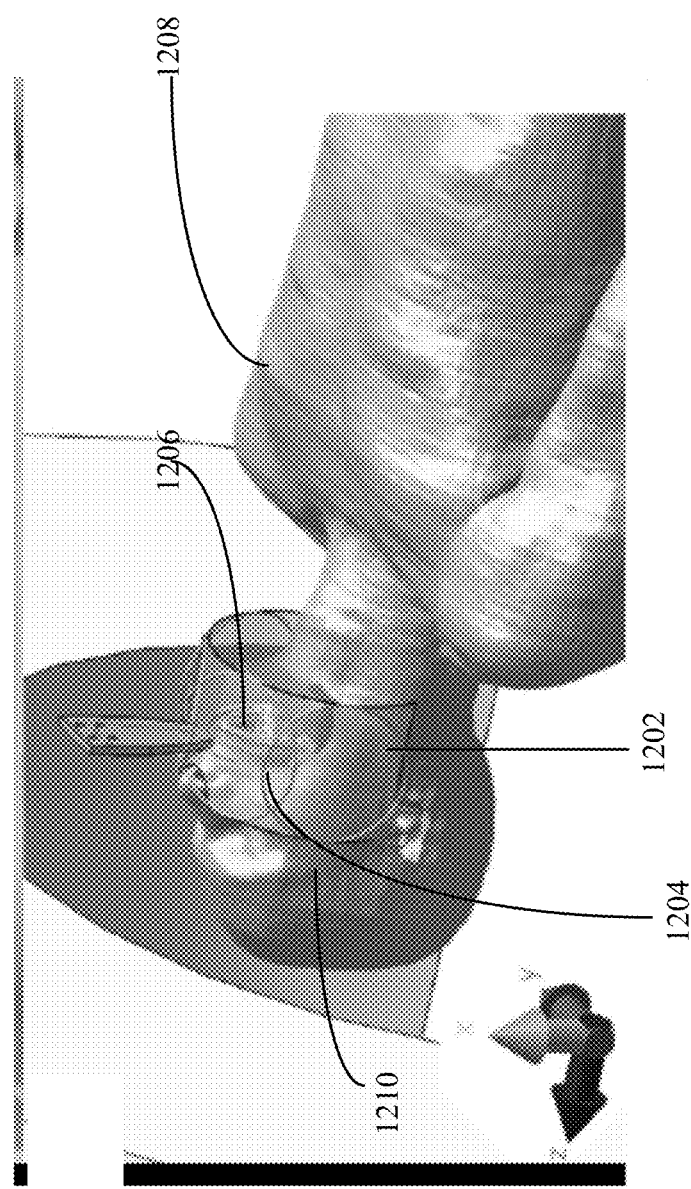
FIG. 12 is a perspective view of an RF coil apparatus including a multi-planar intraoral radio frequency (RF) coil and an extraoral RF coil in accordance with an embodiment.

The multi-planar intraoral coils 700, 800, 900, 1000 and 1100 may be used as transmit-only coils, receive-only coils or transmit and receive coils. In the embodiments described above, the multi-planar combination of coil (or conductor) elements in the form of an impression tray increases the depth of sensitivity. The various embodiments of the multi-planar dipole intraoral RF coil 700, 800, 900, 1000 and 1100 described above with respect to FIGS. 7-11 may provide uniform sensitivity over the teeth and surrounding tissues. The increased penetration depth provides by the multi-planar loop intraoral RF coils described above allows, for example, sensitive detection of the signal from dental roots. In other embodiments, the multi-planar loop intraoral RF coils may minimize coupling with exterior receive coil elements In other embodiments, a multi-planar intraoral RF coil, loop or dipole, may be used in combination with an extraoral RF coil as shown in FIG. 12. In FIG. 12, an extraoral RF coil 1202 having a plurality of loops 1204 is positioned on a surface (e.g., the face) of a patient 1208 and a multi-planar intraoral RF coil (loop or dipole) 1206 is positioned in the occlusal plane between the upper jaw and the lower jaw. The extraoral RF col may be for example, a transmission line resonator, such as, for example, a flexible transmission line resonator (i.e., shielded loop resonators (SLR)). In another embodiment, the multi-planar intraoral RF coil 1206 is a dipole coil. The use of a combination of a multi-planar intraoral RF coil 1206 with an extraoral RF coil 1202 may gain more penetration for face imaging while having less coupling between coil elements. In an embodiment, the multi-planar intraoral RF coil 1206 may be used as a transmit coil and the extraoral RF coil 1202 may be used as a receive coil. The combination of the extraoral RF coil 1202 and a multi-planar dipole intraoral RF coil 1206 may result in improved SNR, improved patient comfort, and small FOVs that can be used with conventional pulse sequence protocols.

Figure 14:
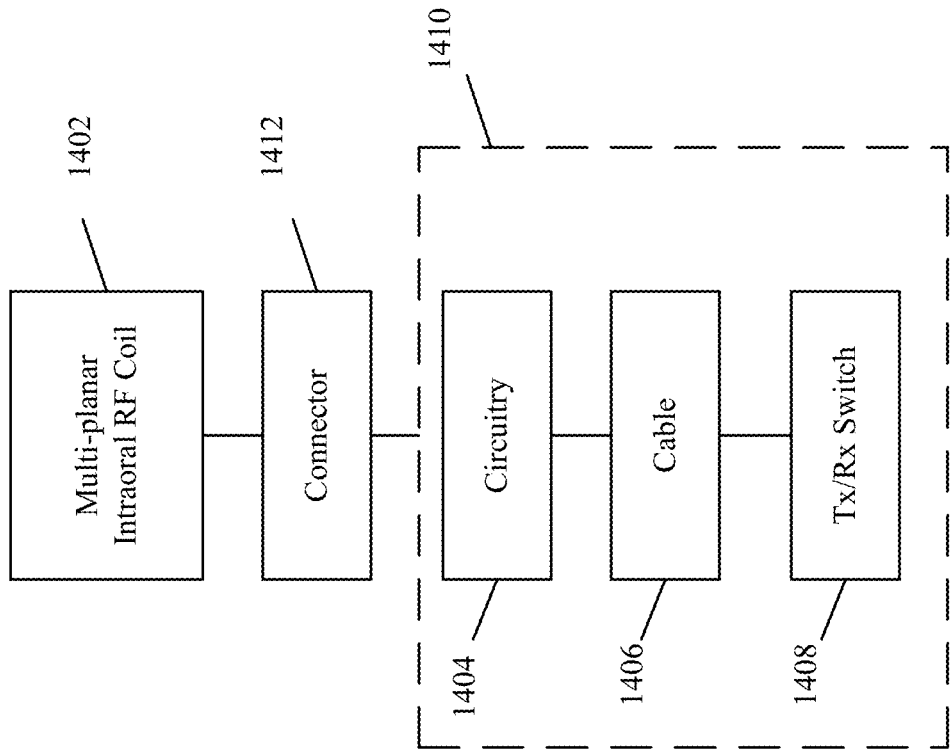
FIG. 14 is a block diagram of a multi-planar RF coil apparatus in accordance with an embodiment.
Figure 13:
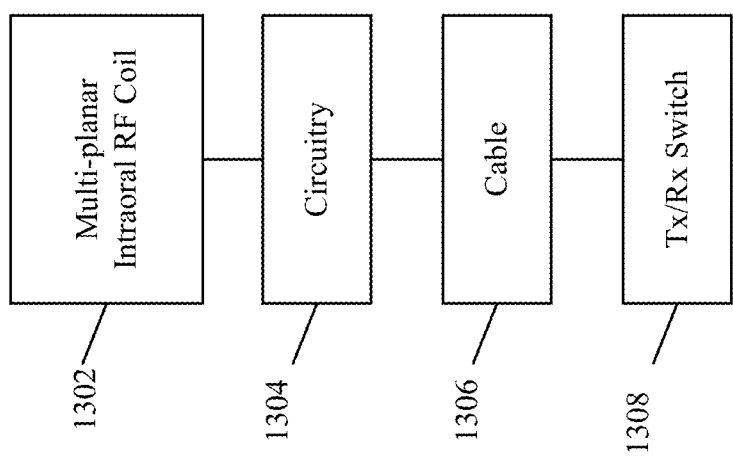
FIG. 13 is block diagram of a multi-planar RF coil apparatus in accordance with an embodiment.

As mentioned, the various embodiments of multi-planar RF coils (loop and dipole) discussed above may be coupled to a cable and other circuitry. FIGS. 13 and 14 are block diagrams of a multi-planar RF coil apparatus in accordance with various embodiments. In FIG. 13, the multi-planar intraoral RF coil 1302 is coupled to circuitry 1304 (e.g., tuning and matching circuitry), one or more cables 1306 and a transmit/receive switch 1306. In an embodiment, the multi-planar intraoral RF coil 1302 is a loop coil. In this embodiment, capacitive tuning and matching circuitry 1304 may be used. In an embodiment, the multi-planar intraoral RF coil 1302 is a dipole coil. In this embodiment, inductive tuning and capacitive matching 1304 may be used. In an embodiment, both the multi-planar intraoral loop and the dipole coil may be interfaced to an Mill system (e.g., Mill system 100 shown in FIG. 1).via the transmit/receive switch 1306. There are several challenges to produce a re-usable multi-planar intraoral RF coil. For example, the coils must allow for easy disinfection without damaging the isolation layers For ease of use, the multi-planar intraoral RF coil may be designed as two parts as shown in FIG. 14. In FIG. 14, the multi-planar intraoral RF coil apparatus includes a dipole part 1402 (the dipole coil elements) and a circuitry part 1410 that are connected via a connector 1412. The connector 1410 is configured so that the coil 1402 can be separated from the circuitry 1404, cable 1406 and transmit/receive switch 1408. Accordingly, the circuitry 1410 can be re-usable, whereas the dipole part 1402 can be disposed after in vivo use. As mentioned, the RF cols 1302, 1402 may be coupled to one or more cables 1306, 1406. In an embodiment, the cable(s) 1306, 1406 may be shielded, for example, by designing the cables 1306, 1406 as embedded coplanar or parallel strip lines or wires to minimize unbalanced currents and reduce E fields.

The present invention has been described in terms of one or more preferred embodiments, and it should be appreciated that many equivalents, alternatives, variations, and modifications, aside from those expressly stated, are possible and within the scope of the invention.

The invention claimed is:

1. A multi-planar intraoral radio frequency (RF) coil apparatus for use in a magnetic resonance imaging system, the RF coil apparatus comprising:
a single housing having a shape configured to be positioned in an occlusal plane between an upper jaw and a lower jaw of a subject; and
a plurality of RF coil elements disposed within the housing, the plurality of RF coil elements comprising:
a first RF coil element positioned in a first plane substantially parallel to the occlusal plane; and
a second RF coil element positioned in a second plane different from the first plane and substantially parallel to the first plane and the occlusal plane;
wherein the plurality of RF coil elements are configured to form at least one channel that is configured to receive one or more teeth of the upper jaw and one or more teeth of the lower jaw of the subject.

2. The multi-planar intraoral RF coil according to claim 1, wherein the plurality of RF coil elements are loop coils and the second RF coil element is positioned above the first RF coil element in the housing.

3. The multi-planar intraoral RF coil according to claim 2, wherein the plurality of RF coil elements further comprises a third RF coil element positioned in a third plane different from the first plane and the second plane and substantially parallel to the first plane, the second plane, and the occlusal plane, the third RF coil element positioned below the first RF coil element in the housing.

4. The multi-planar intraoral RF coil according to claim 1, wherein the plurality of RF coil elements are dipole coil elements.

5. The multi-planar intraoral RF coil according to claim 4, wherein second RF coil element is positioned above the first RF coil element in the housing.

6. The multi-planar intraoral RF coil according to claim 5, wherein the plurality of RF coil elements further comprises a third RF coil element positioned in a third plane different from the first plane and the second plane and substantially parallel to the first plane, the second plane, and the occlusal plane, the third RF coil element positioned below the first RF coil element in the housing.

7. The multi-planar intraoral RF coil according to claim 6, further comprising a first dipole arm and a second dipole arm, wherein the first RF coil element, the second RF coil element and the third RF coil element are disposed within the first dipole arm and the second dipole arm.

8. The multi-planar intraoral RF coil according to claim 7, wherein a distal end of the first dipole arm includes a high permittivity material and a distal end of the second dipole arm includes a high permittivity material.

9. The multi-planar intraoral RF coil according to claim 7, wherein the at least one channel includes a first channel configured to receive the one or more teeth of the upper jaw of the subject and a second channel configured to receive the one or more teeth of the lower jaw of the subject, wherein the first dipole arm includes the first channel and the second channel.

10. A radio frequency (RF) coil apparatus for use in a magnetic resonance imaging system, the RF coil apparatus comprising:
an extraoral RF coil configured to be positioned on a surface of a subject; and
a multi-planar intraoral RF coil comprising:
a single housing having a shape configured to be positioned in an occlusal plane between an upper jaw and a lower jaw of the subject; and
a plurality of RF coil elements disposed within the housing, the plurality of RF coil elements comprising:
a first RF coil element positioned in a first plane substantially parallel to the occlusal plane; and
a second RF coil element positioned in a second plane different from the first plane and substantially parallel to the first plane and the occlusal plane;

wherein the plurality of RF coil elements are configured to form at least one channel that is configured to receive one or more teeth of the upper jaw and one or more teeth of the lower jaw of the subject.

11. The RF coil apparatus according to claim 10, wherein the extraoral RF coil is a shielded loop resonator.

12. The RF coil apparatus according to claim 11, wherein the plurality of RF coil elements are dipole coil elements.

13. The RF coil apparatus according to claim 12, wherein the extraoral RF coil is a receive coil and the multi-planar intraoral RF coil is a transmit coil.

14. A magnetic resonance imaging (MRI) system comprising:
   a magnet system configured to generate a polarizing magnetic field about at least a portion of a subject;
   a magnetic gradient system including a plurality of magnetic gradient coils configured to apply at least one magnetic gradient field to the polarizing magnetic field; and
   a radio frequency (RF) system configured to apply an RF field to the subject and to receive magnetic resonance signals from the subject using at least one RF coil, wherein the at least one RF coil is a multi-planar intraoral RF coil comprising:
      a single housing having a shape configured to be positioned in an occlusal plane between an upper jaw and a lower jaw of the subject; and
      a plurality of RF coil elements disposed within the housing, the plurality of RF coil elements comprising:
         a first RF coil element positioned in a first plane substantially parallel to the occlusal plane; and
         a second RF coil element positioned in a second plane different from the first plane and substantially parallel to the first plane and the occlusal plane;
      wherein the plurality of RF coil elements are configured to form at least one channel that is configured to receive one or more teeth of the upper jaw and one or more teeth of the lower jaw of the subject.

15. The MRI system according to claim 14, wherein the plurality of RF coil elements are loop coils.

16. The MRI system according to claim 14, wherein the plurality of RF coil elements are dipole coil elements.

17. The MRI system according to claim 14, wherein the magnet system is cylindrical and the polarizing magnetic field is oriented along a longitudinal axis of an imaging volume defined by the magnet system.

18. The MRI system according to claim 14, wherein the polarizing magnetic field is vertically oriented with respect to the magnet system.

* * * * *

UNITED STATES PATENT AND TRADEMARK OFFICE
CERTIFICATE OF CORRECTION

PATENT NO. : 11,448,714 B2
APPLICATION NO. : 16/933855
DATED : September 20, 2022
INVENTOR(S) : Donald Robert Nixdorf et al.

It is certified that error appears in the above-identified patent and that said Letters Patent is hereby corrected as shown below:

In the Specification

Column 1, Line 66, "MM" should be --MRI--.

Column 2, Line 8, "MM" should be --MRI--.

Column 2, Line 37, "MM" should be --MRI--.

Column 4, Line 40, "Mill system 100. Mill" should be --MRI system 100. MRI--.

Column 5, Line 8, "MM" should be --MRI--.

Column 6, Line 5, "("MIRA")" should be --("MRA")--.

Column 6, Line 63, "MM" should be --MRI--.

Column 7, Line 34, "MM" should be --MRI--.

Column 12, Line 12, "(er)" should be --($e_r$)--.

Column 12, Line 44, "MM-visible" should be --MRI-visible--.

Column 13, Line 33, "Mill system (e.g., Mill" should be --MRI system (e.g., MRI--.

Signed and Sealed this
Tenth Day of January, 2023

Katherine Kelly Vidal
*Director of the United States Patent and Trademark Office*